(12) United States Patent
Zhang et al.

(10) Patent No.: US 10,535,509 B2
(45) Date of Patent: Jan. 14, 2020

(54) ION MIGRATION TUBE AND METHOD OF OPERATING THE SAME

(71) Applicants: Nuctech Company Limited, Beijing (CN); Tsinghua University, Beijing (CN)

(72) Inventors: Qingjun Zhang, Beijing (CN); Yuanjing Li, Beijing (CN); Ziran Zhao, Beijing (CN); Weiping Zhu, Beijing (CN); Huishao He, Beijing (CN); Xianghua Li, Beijing (CN); Qiufeng Ma, Beijing (CN)

(73) Assignees: Nuctech Company Limited, Beijing (CN); Tsinghua University, Beijing (CN)

( * ) Notice: Subject to any disclaimer, the term of this patent is extended or adjusted under 35 U.S.C. 154(b) by 76 days.

(21) Appl. No.: 15/858,255

(22) Filed: Dec. 29, 2017

(65) Prior Publication Data

US 2018/0190482 A1    Jul. 5, 2018

(30) Foreign Application Priority Data

Dec. 29, 2016  (CN) .......................... 2016 1 1270479

(51) Int. Cl.
   *G01N 27/62* (2006.01)
   *H01J 49/06* (2006.01)
   *H01J 49/42* (2006.01)
(52) U.S. Cl.
   CPC .......... *H01J 49/063* (2013.01); *G01N 27/622* (2013.01); *H01J 49/42* (2013.01)
(58) Field of Classification Search
   CPC .. H01J 49/00; H01J 49/02; H01J 49/06; H01J 49/061; H01J 49/062; H01J 49/063; H01J 49/066

(Continued)

(56) References Cited

U.S. PATENT DOCUMENTS

2004/0031920 A1*  2/2004  Giles ................... G01N 27/622
                                                              250/287
2008/0179515 A1   7/2008  Sperline
                (Continued)

FOREIGN PATENT DOCUMENTS

CN    101728208 A    6/2010
CN    102313774 A    1/2012
            (Continued)

OTHER PUBLICATIONS

"Chinese Application Serial No. 201611270479.6, Office Action dated Jan. 11, 2018", w/ English Translation, (Jan. 11, 2018), 19 pgs.

(Continued)

*Primary Examiner* — Jason L McCormack
(74) *Attorney, Agent, or Firm* — Schwegman Lundberg & Woessner, P.A.

(57) ABSTRACT

The present disclosure provides an ion migration tube and a method of operation the same. The ion migration tube includes an interior space and an ion gate disposed within the interior space, the interior space includes an ionization region having an absolute value of potential V1 and a migration region. An ion gate is disposed between the ionization region and the migration region and includes a first ion gate grid having an absolute value of potential V2 and a second ion gate grid having an absolute value of potential V3, the migration region comprises at least a first migration region electrode having an absolute value of potential V4 and a second migration region electrode having an absolute value of potential V5. When the ion gate is opened, a potential well is formed for ionized ions between the first ion gate grid and the first migration region electrode so as to compress an ion group entering the migration region.

9 Claims, 2 Drawing Sheets

(58) Field of Classification Search
USPC .......................... 250/281, 282, 283, 290, 293
See application file for complete search history.

(56) References Cited

U.S. PATENT DOCUMENTS

| | | |
|---|---|---|
| 2010/0230588 A1 | 9/2010 | Atkinson et al. |
| 2013/0292562 A1* | 11/2013 | Clemmer ............. G01N 27/622 |
| | | 250/282 |
| 2015/0188295 A1 | 7/2015 | Zhang et al. |

FOREIGN PATENT DOCUMENTS

| | | |
|---|---|---|
| CN | 102931046 A | 2/2013 |
| CN | 102903598 B | 4/2015 |
| CN | 206349332 U | 7/2017 |
| JP | 2009259465 A | 11/2009 |

OTHER PUBLICATIONS

"Chinese Application Serial No. 201611270479.6, Office Action dated Feb. 28, 2019", w/ English Translation, (Feb. 28, 2019), 11 pgs.

"Chinese Application Serial No. 201611270479.6, Office Action dated Sep. 14, 2018", w/ English Translation, (Sep. 14, 2018), 22 pgs.

"European Application Serial No. 17211140.3, Extended European Search Report dated May 14, 2018", (May 14, 2018), 7 pgs.

* cited by examiner

ION MIGRATION TUBE AND METHOD OF OPERATING THE SAME

CROSS-REFERENCE TO RELATED APPLICATION

The present application claims priority to Chinese Patent Application No. 201611270479.6, filed on Dec. 29, 2016, entitled "ION MIGRATION TUBE AND METHOD OF OPERATING THE SAME", which is incorporated herein by reference in its entirety.

TECHNICAL FIELD

The present disclosure relates to the field of ion migration tube technologies, and particularly, to an ion migration tube and a method of operating an ion migration tube.

DESCRIPTION OF THE RELATED ART

Ion mobility spectrum (IMS) has become a maturer on-site trace detection technique in molecular level. A key component of an ion mobility spectrometer is an ion migration tube. In the migration tube, sample molecules may produce corresponding, relatively stable product ions under the action of an ionization source by means of proton acquisition, electron attachment, electron exchange or the like. The product ions enter and drift in a migration region in batches almost at the same time under control of an ion gate. In a constant electric field in the atmosphere environment, these product ions behave macroscopically as obtaining a constant average speed due to being subject to acceleration under the electric field and deceleration due to collision among drifting neutral gas molecules. Since the product ions have different specific charges, geometric configurations and collision sections, the average speeds obtained by the product ions vary, thus, the product ions will be separated after passing through a section of electric field, and successively reaches a detector and thereby are detected.

Ion mobility spectrometer has been widely applied in fields such as detection of explosives, screening of drugs, early warning of chemical warfare agent and the like due to its advantages such as a high sensitivity, a fast analysis speed, a low cost, a simple structure, portability and the like. However, a lower resolution is one bottleneck in application and development of the ion mobility spectrum.

SUMMARY

According to an aspect of the present disclosure, there is provided an ion migration tube, comprising an interior space and an ion gate disposed within the interior space and configured to be opened or closed, the interior space comprising an ionization region having an absolute value of potential V1 and a migration region isolated from the ionization region by the ion gate, so that matters enters the ion migration tube from one end of the ionization region, are ionized within the ionization region and then are driven by an electric field to enter the migration region:

wherein, the ion gate disposed between the ionization region and the migration region comprises a first ion gate grid having an absolute value of potential V2 and a second ion gate grid having an absolute value of potential V3, the first ion gate grid and the second ion gate grid are parallel to each other and spaced apart from each other by an insulation sheet so as to divide the ion migration tube into the ionization region and the migration region; the migration region comprises at least a first migration region electrode having an absolute value of potential V4 and a second migration region electrode having an absolute value of potential V5, and the second migration region electrode is farther from the second ion gate grid than the first migration region electrode; and wherein when the ion gate is opened, a potential well is formed for ionized ions between the first ion gate grid and the first migration region electrode so as to compress an ion group entering the migration region.

In an embodiment, when the ion gate is opened, the absolute value of potential V2 of the first ion gate grid is larger than the absolute value of potential V4 of the first migration region electrode, the absolute value of potential V4 of the first migration region electrode is larger than the absolute value of potential V3 of the second ion gate grid, and the absolute value of potential V3 of the second ion gate grid is larger than or equal to the absolute value of potential V5 of the second migration region electrode.

In an embodiment, when the ion gate is opened, the absolute value of potential V2 of the first ion gate grid and the absolute value of potential V1 of the ionization region are kept constant, and the second ion gate grid is applied with a reverse pulse potential, such that the absolute value of potential V3 of the second ion gate grid is reduced by one pulse in absolute value of potential.

In an embodiment, when the ion gate is opened, absolute values of potential of electrodes of the migration region, including a first migration region electrode and a second migration region electrode, are kept the same as those in case the ion gate is closed.

In an embodiment, in case the ion gate is kept closed, the ion migration tube is configured such that the absolute value of potential V1 of the ionization region is larger than or equal to the absolute value of potential V3 of the second ion gate grid, the absolute value of potential V3 of the second ion gate grid is larger than the absolute value of potential V2 of the first ion gate grid, the absolute value of potential V2 of the first ion gate grid is larger than the absolute value of potential V4 of the first migration region electrode, and the absolute value of potential V4 of the first migration region electrode larger than the absolute value of potential V5 of the second migration region electrode.

In an embodiment, in case the ion gate is kept closed, the absolute value of potential V3 of the second ion gate grid is higher by 7~30 volts than the absolute value of potential V2 of the first ion gate grid, and a difference between the absolute value of potential V3 of the second ion gate grid and the absolute value of potential V1 of the ionization region is not greater than 50 volts.

Another aspect of the present disclosure provided a method of operating an ion migration tube, wherein the ion migration tube comprises an interior space and an ion gate disposed within the interior space and configured to be opened or closed, the interior space comprises an ionization region having an absolute value of potential V1 and a migration region isolated from the ionization region by the ion gate, so that matters enters the ion migration tube from one end of the ionization region, are ionized within the ionization region and then are driven by an electric field to enter the migration region;

wherein, the ion gate disposed between the ionization region and the migration region comprises a first ion gate grid having an absolute value of potential V2 and a second ion gate grid having an absolute value of potential V3, the first ion gate grid and the second ion gate grid are parallel to each other and spaced apart from each other by an insulation sheet so as to divide the ion migration tube into the ionization region and the migration region; the migration region comprises at least a first migration region electrode having an absolute value of potential V4 and a second migration region electrode having an absolute value of potential V5, and the second migration region electrode is farther from the second ion gate grid than the first migration region electrode; and wherein the method comprises, when the ion gate is opened, forming a potential well for ionized ions between the first ion gate grid and the first migration region electrode so as to compress an ion group entering the migration region.

In an embodiment, when the ion gate is opened, the absolute value of potential V2 of the first ion gate grid and the absolute value of potential V1 of the ionization region are kept constant, and the second ion gate grid is applied with a reverse pulse potential, such that the absolute value of potential V3 of the second ion gate grid is reduced by one pulse in absolute value of potential, thereby the absolute value of potential V2 of the first ion gate grid larger than the absolute value of potential V4 of the first migration region electrode, the absolute value of potential V4 of the first migration region electrode larger than the absolute value of potential V3 of the second ion gate grid, the absolute value of potential V3 of the second ion gate grid larger than or equal to the absolute value of potential V5 of the second migration region electrode.

In an embodiment, when the ion gate is opened, absolute values of potential of electrodes of the migration region, including a first migration region electrode and a second migration region electrode, are kept the same as those in case the ion gate is closed.

In an embodiment, in case the ion gate is kept closed, the ion migration tube is operated such that the absolute value of potential V1 of the ionization region is larger than or equal to the absolute value of potential V3 of the second ion gate grid, the absolute value of potential V3 of the second ion gate grid is larger than the absolute value of potential V2 of the first ion gate grid, the absolute value of potential V2 of the first ion gate grid is larger than the absolute value of potential V4 of the first migration region electrode, and the absolute value of potential V4 of the first migration region electrode larger than the absolute value of potential V5 of the second migration region electrode.

In an embodiment, in case the ion gate is kept closed, the absolute value of potential V3 of the second ion gate grid is higher by 7~30 volts than the absolute value of potential V2 of the first ion gate grid, and a difference between the absolute value of potential V3 of the second ion gate grid and the absolute value of potential V1 of the ionization region is not greater than 50 volts.

DETAILED DESCRIPTION OF PREFERRED EMBODIMENTS

Technique schemes of the present disclosure will be described in detail hereinafter in combination with exemplary embodiments with reference to the drawings. In the description, same or similar component is indicated by same or similar reference number. Description of the embodiments of the present disclosure with reference to the drawings tends to describe general concepts of the disclosure and should not be understood to limit the present disclosure.

In addition, in the description as below, much specific detail is described to provide comprehensive understanding of the embodiments of the present disclosure for ease of presentation. However, it is obvious one or more embodiments may be implemented without the detail. In other situation, known structure and device are shown by means of diagrammatic presentation to simplify the accomplish drawings.

Figure 1:
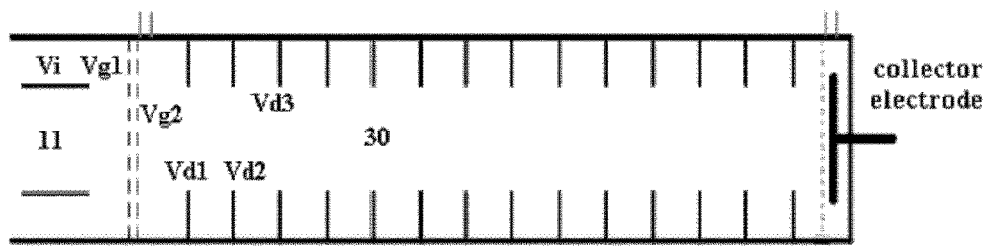
FIG. 1 is a schematic diagram showing an ion migration tube according to an embodiment of the present disclosure.

A conventional ion migration tube is mainly consisted of three components including an ionization region 11, a migration region 30 and a detector, as shown in FIG. 1. In an example, the ionization region 11 is isolated from the migration region 30 by using an ion gate. The migration region 30 and the detector are isolated from each other by the ion gate. The ion gate is generally formed of two gate grids spaced apart from each other or closely adjacent to each other, and these two gate grids are isolated from each other by an insulation sheet. The gate grid may be a gate grid made of metal thin wires, and the insulation sheet is provided between the two gate grids.

In FIG. 1, Vi is an ionization region voltage, Vg1 is a voltage on a first gate grid electrode, Vg2 is a voltage on a second ion gate grid electrode, which is also a voltage at a starting end of the migration region 30 (that is, the highest voltage in the migration region 30), voltages on respective electrodes in the migration region 30 are formed by resistive dividers, and a tube housing and a collector electrode each have a zero potential. In case the ion gate is closed, absolute values of the voltages on the respective electrodes are respectively represented as |Vi|=V1, |Vg1|=V2, |Vg2|=V3, |Vd1|=V4, and |Vd2|=V5, which meet the following amplitude relationship: V1>V3>V2>V4>V5, where a voltage difference between V4 and V5 is about 75V. Obviously, when the ion gate is closed, there is an electric field between the electrodes of the two ion gate grids, which has a direction opposite to that of the electric field in the migration region 30, so that ions cannot pass through the ion gate.

In the conventional ion migration tube, at the moment the ion gate is opened, the Vg1 will be applied with a pulse having the same polarity as that of the previous voltage and an amplitude ΔV, such that (V2+ΔV)>V3>V4>V5. At the moment the ion gate is opened, the opposite electric field between the electrodes of the two ion gate grids is rectified such that the ions are allowed to pass through the ion gate.

In an operating mode of the conventional ion migration tube, ion groups entering the migration region 30 during the ion gate is opened are rendered with different flight speeds due to different position and potentials of ions in the initial state and thus have different flight times, which will finally lead to a wide spectral peak half height width, thereby reducing the resolution of the ion mobility spectrometer.

In an embodiment of the present disclosure, there is provided an ion migration tube, comprising an interior space and an ion gate disposed within the interior space and configured to be opened or closed, the interior space comprising an ionization region 11 having an absolute value of potential V1 and a migration region 30, matters enters the ion migration tube from one end of the ionization region 11, are ionized within the ionization region 11 and then are driven by an electric field to enter the migration region 30. An ion gate is disposed between the ionization region 11 and the migration region 30 and comprises a first ion gate grid having an absolute value of potential V2 and a second ion gate grid having an absolute value of potential V3, the first ion gate grid and the second ion gate grid are parallel to each other and spaced apart from each other by an insulation sheet so as to divide the ion migration tube into the ionization region 11 and the migration region 30; the migration region 30 comprises at least a first migration region electrode 31 having an absolute value of potential V4 and a second migration region electrode 32 having an absolute value of potential V5, and the second migration region electrode 32 is farther from the second ion gate grid than the first migration region electrode 31. According to this embodiment, when the ion gate is opened, a potential well is formed for ionized ions between the first ion gate grid and the first migration region electrode so as to compress an ion group entering the migration region 30.

In this embodiment, when the ion gate is opened, the absolute value of potential V2 of the first ion gate grid is larger than the absolute value of potential V4 of the first migration region electrode 31, the absolute value of potential V4 of the first migration region electrode 31 is larger than the absolute value of potential V3 of the second ion gate grid, and the absolute value of potential V3 of the second ion gate grid is larger than or equal to the absolute value of potential V5 of the second migration region electrode 32, that is, V2>V4>V3≥V5. In an example, a voltage amplitude of the reverse electric field between the voltage V3 of the second gate grid and the voltage V2 of the first gate grid is 7V~30V, and a potential difference between the second ion gate grid and the ionization region 11 is not greater than 50 volts.

As such, it can be ensured that there are sufficient ions to enter the migration region 30 when the ion gate is opened, so as to ensure sensitivity of the mobility spectrometer; on the other hand, it can also be ensured that no ion leakage when the gate is closed. Further, a potential barrier will be formed between the second ion gate and the second migration electrode when the ion gate is opened, such that ions firstly entering the migration region 30 will be decelerated by the potential barrier, achieving compression of the ion group, and acceleration of the ion group is recovered by migration electric field after the ion gate is closed.

According to embodiments of the present disclosure, during a limited opening time of the ion gate, an ion group having an initial position close to the second gate grid of the ion gate (that is, having an anterior position) will firstly enter the migration region, and is decelerated in the potential well formed between the ion gate system (including the first gate grid and the second gate grid) and the first two stages of migration region electrodes (first and second migration region electrodes), while an ion group having a posterior initial position will subsequently enter the migration region and will be decelerated in the potential well within a time period shorter than the ion group firstly entering the migration region or is not decelerated, thereby total ion groups entering the migration region are compressed, improving the resolution of the migration tube.

According to this embodiment, when the ion gate is opened, the absolute value of potential V2 of the first ion gate grid and the absolute value of potential V1 of the ionization region 11 may be kept constant, and the second ion gate grid is applied with a reverse pulse potential, such that the absolute value of potential V3 of the second ion gate grid is reduced by one pulse in absolute value of potential. That is, a pulse voltage which would otherwise applied to the first ion gate grid Vg1 in prior arts is applied to the second ion gate grid Vg2, and the voltage pulse is reversed, and meanwhile it is kept that first ion gate grid voltage Vg1 is equal to V2 and the ionization region voltage Vi is equal to V1.

According to this embodiment, in the ion migration tube, in case the ion gate is kept closed, the ion migration tube is configured such that the absolute value of potential V1 of the ionization region 11 is larger than or equal to the absolute value of potential V3 of the second ion gate grid, the absolute value of potential V3 of the second ion gate grid is larger than the absolute value of potential V2 of the first ion gate grid, the absolute value of potential V2 of the first ion gate grid is larger than the absolute value of potential V4 of the first migration region electrode 31, and the absolute value of potential V4 of the first migration region electrode larger than the absolute value of potential V5 of the second migration region electrode 32, that is, V1≥V3>V2>V4>V5. According to this embodiment, when the ion gate is opened, when the ion gate is opened, the absolute values V4, V5 of potential of the electrodes, including the first migration region electrode 31 and the second migration region electrode 32, are kept the same as those in case the ion gate is closed. Absolute values of potential of other electrodes of the migration region 30 are kept the same as those in case the ion gate is closed. Specifically, in an embodiment, in ion migration tube, in case the ion gate is kept closed, the absolute value of potential V3 of the second ion gate grid is higher by 7~30 volts than the absolute value of potential V2 of the first ion gate grid, and a difference between the absolute value of potential V3 of the second ion gate grid and the absolute value of potential V1 of the ionization region 11 is not greater than 50 volts.

With the ion migration tube according to embodiments of the present disclosure, the resolution of the migration tube is increased by about 5~10% when compared to the ion migration tube having a conventional configuration in prior arts.

An embodiment of the present disclosure further provides a method of operating an ion migration tube, wherein the ion migration tube comprises an interior space and an ion gate which is disposed within the interior space and configured to be opened or closed, the interior space comprises an ionization region 11 having an absolute value of potential V1 and a migration region 30, and matters, which enters the ion migration tube from one end of the ionization region 11, are ionized within the ionization region 11 and then are driven by an electric field to enter the migration region 30; wherein, an ion gate disposed between the ionization region 11 and the migration region 30 comprises a first ion gate grid having an absolute value of potential V2 and a second ion gate grid having an absolute value of potential V3, the first ion gate grid and the second ion gate grid are parallel to each other and spaced apart from each other by an insulation sheet so as to divide the ion migration tube into the ionization region 11 and the migration region 30; the migration region 30 comprises at least a first migration region electrode 31 having an absolute value of potential V4 and a second migration region electrode 32 having an absolute value of potential V5, and the second migration region electrode 32 is farther from the second ion gate grid than the first migration region electrode 31; and wherein the method comprises, when the ion gate is opened, forming a potential well for ionized ions between the first ion gate grid and the first migration region electrode 31 so as to compress an ion group entering the migration region 30.

In the method according to an embodiment of the present disclosure, when the ion gate is opened, the absolute value of potential V2 of the first ion gate grid and the absolute value of potential V1 of the ionization region 11 are kept constant, and the second ion gate grid is applied with a reverse pulse potential, such that the absolute value of potential V3 of the second ion gate grid is reduced by one pulse in absolute value of potential, thereby the absolute value of potential V2 of the first ion gate grid larger than the absolute value of potential V4 of the first migration region electrode 31, the absolute value of potential V4 of the first migration region electrode larger than the absolute value of potential V3 of the second ion gate grid, the absolute value of potential V3 of the second ion gate grid larger than or equal to the absolute value of potential V5 of the second migration region electrode 32, that is, V2>V4>V3≥V5.

In an example, a voltage amplitude of the reverse electric field between the voltage V3 of the second gate grid and the voltage V2 of the first gate grid is 7V~30V, and a potential difference between the second ion gate grid and the ionization region 11 is not greater than 50 volts.

In the method according to this embodiment, when the ion gate is opened, absolute values of potential of electrodes of the migration region 30, including the first migration region electrode 31 and the second migration region electrode 32, are kept the same as those in case the ion gate is closed.

In the method according to this embodiment, in case the ion gate is kept closed, the ion migration tube is operated such that the absolute value of potential V1 of the ionization region 11 is larger than or equal to the absolute value of potential V3 of the second ion gate grid, the absolute value of potential V3 of the second ion gate grid is larger than the absolute value of potential V2 of the first ion gate grid, the absolute value of potential V2 of the first ion gate grid is larger than the absolute value of potential V4 of the first migration region electrode 31, and the absolute value of potential V4 of the first migration region electrode larger than the absolute value of potential V5 of the second migration region electrode 32, that is, V1≥V3>V2>V4>V5.

A specific example of the ion migration tube and a detection result of resolution thereof will be described below.

Figure 2:
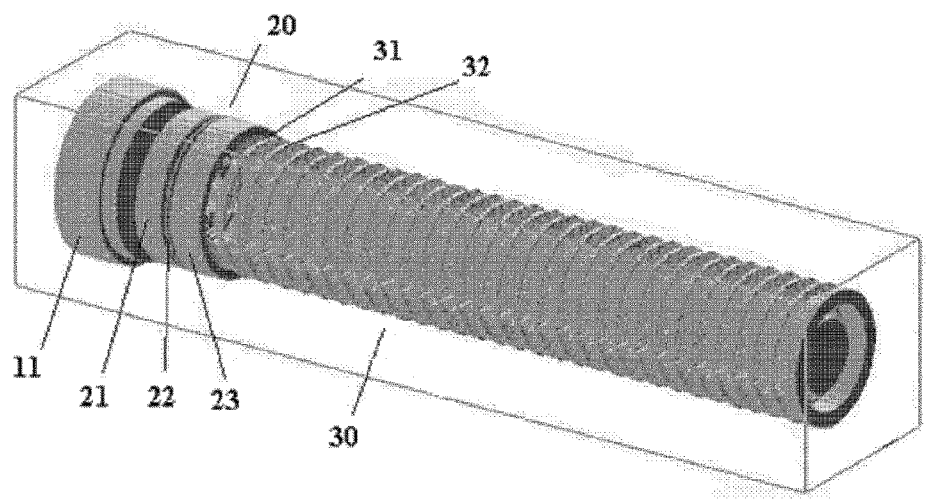
FIG. 2 is a diagram of a model modeled by Simion software for a conventional migration tube.

FIG. 2 shows a model modeled by using for example Simion software according to structure and size of a conventional migration tube, where the migration region 30 has a length of 88 mm, a voltage across two ion gate grids of the ion gate is 20V, a distance between the two ion gate grids is set as 0.5 mm, and an electric field intensity of the migration region 30 is set as 260V/cm.

In a conventional way of opening the ion gate, when the ion gate is closed, V3>V2, and there is an electric field having a direction opposite to that of the electric field in the migration region 30, so that ions cannot pass through the ion gate. At the moment the ion gate is opened, the first gate grid electrode Vg1 will be applied with a pulse having the same polarity as that of its previous voltage and an amplitude ΔV, such that (V2+ΔV)>V3, and the opposite electric field between the two ion gate grids is changed, such that the ions are allowed to pass through the ion gate. The ion group enters the migration region 30 under action of a forward electric field of the ion gate, and passes through the ion gate grids under a weak electric field in the migration region 30 and reverse collision from a migration gas flow, reaches a Faraday disc and thereby is collected.

Figure 3:
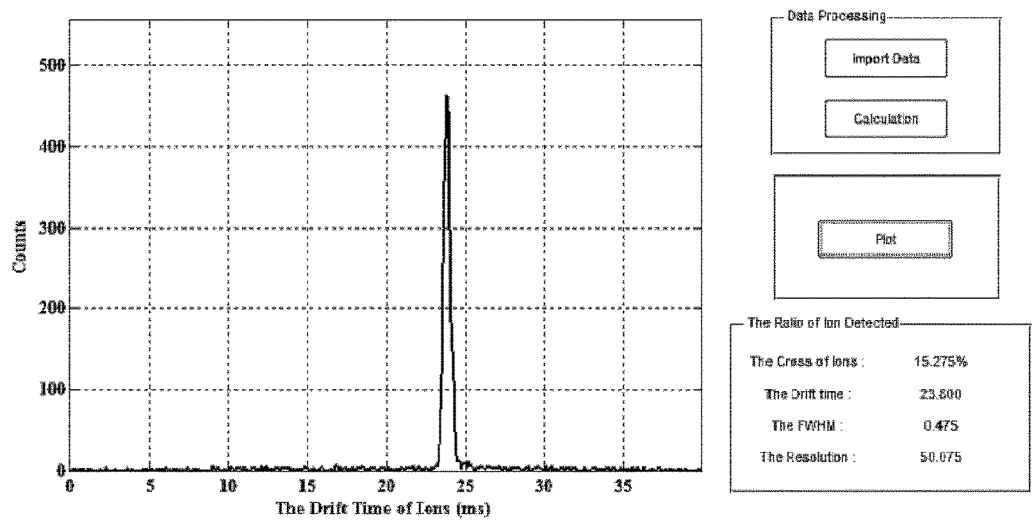
FIG. 3 is a diagram showing an ion mobility spectrum obtained by operating 10000 instances in a model of a migration tube modeled by Simion software in a conventional operating mode.

FIG. 3 shows a mobility spectrogram obtained by operating 10,000 instances by Simion software in a working state of the conventional ion gate, wherein a time length of opening the ion gate is set as 200 us, and an opening period is 43 ms. It is obtained that the mobility spectrum half peak width is 0.475 ms, the peak position is 23.8 ms, and the resolution is 50.075.

Figure 4:
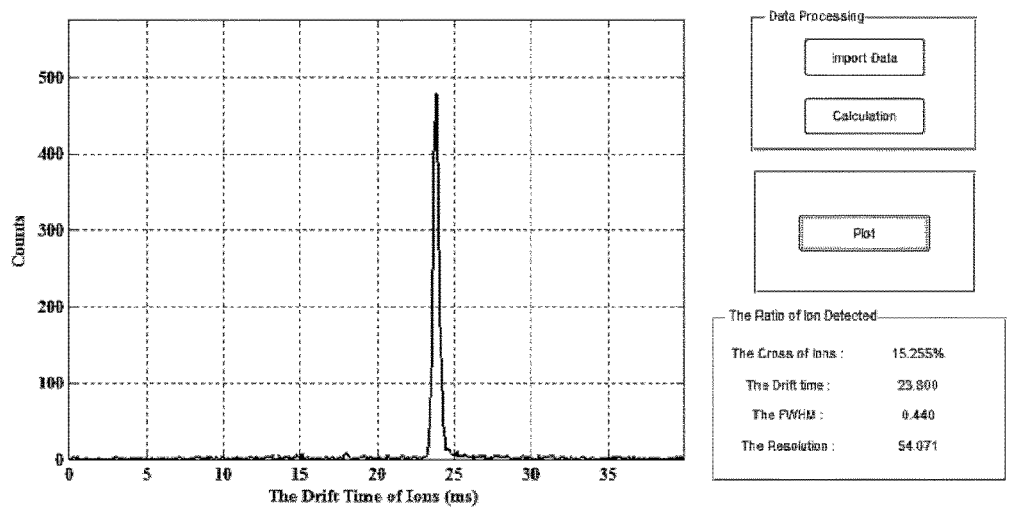
FIG. 4 is a diagram showing an ion mobility spectrum obtained by operating 10000 instances in a model of a migration tube modeled by Simion software in an operating mode according to an embodiment of the present disclosure.

Operating conditions of the Simion software are adjusted, without changing the mechanism of the ion migration tube established by the Simion software, such that the pulse voltage which would otherwise be applied to the first ion gate grid Vg1 is applied to the second ion gate grid Vg2 and the voltage pulse is reversed, and meanwhile it is kept that the first ion gate grid voltage Vg1 is equal to V2 and the ionization region voltage Vi is equal to V1. When the gate is closed, V2<V3, and there is an electric field between the electrodes of the two ion gate grids, which has a direction opposite to that of the electric field in the migration region 30, so that ions cannot pass through the ion gate; when the ion gate is opened, V2>V4>V3≥V5, the reversed electric field between the ion gate grids is changed such that the ions are allowed to pass through the ion gate. After the ions reach the migration region 30, the ion group reaching the migration region 30 will be compressed under the action of the opposite electric field since the second ion gate grid voltage V3 is less than the first migration electrode voltage V4. After the ion gate is closed, the migration electric field recovers to normal, and the ion group migrates at a constant speed under actions of the migration electric field and the migration gas flow. FIG. 4 shows a mobility spectrogram obtained by operating 10,000 instances by Simion software in case the way of opening the ion gate is modified according to the present disclosure, wherein a time length of opening the ion gate is set as 200 us, and an opening period is 43 ms. It is obtained that the mobility spectrum half peak width is 0.440 ms, the peak position is 23.8 ms, and the resolution is 54.071.

As can be seen from calculation that after adjusting, according to the present disclosure, the way of opening the ion gate of the conventional migration tube without changing the structure of the migration tube, the mobility spectrum half peak width is reduced from 0.475 ms to 0.440 ms. The adjusted way of opening the ion gate has a certain compression effect on the ion group entering the migration region 30, and the migration tube resolution is increased by about 8%. (Advantageous effects include: 1) a small modification, simply implementation; 2) compression, being not only a potential barrier, but also a potential well)

Although several exemplary embodiments according the general concepts of the present disclosure have been shown and described, it would be appreciated by those skilled in the art that various changes or modifications may be made in these embodiments without departing from the principles and spirit of the disclosure, the scope of which is defined in the claims and their equivalents.

What is claimed is:

1. An ion migration tube, comprising an interior space and an ion gate disposed within the interior space and configured to be opened or closed, the interior space comprising an ionization region having an absolute value of potential V1 and a migration region isolated from the ionization region by the ion gate, so that matters which enters the ion migration tube from one end of the ionization region, are ionized within the ionization region and then are driven by an electric field to enter the migration region;
   wherein, the ion gate disposed between the ionization region and the migration region comprises a first ion gate grid having an absolute value of potential V2 and a second ion gate grid having an absolute value of potential V3, the first ion gate grid and the second ion gate grid are parallel to each other and spaced apart from each other by an insulation sheet so as to divide the ion migration tube into the ionization region and the migration region; the migration region comprises at least a first migration region electrode having an absolute value of potential V4 and a second migration region electrode having an absolute value of potential V5, and the second migration region electrode is farther from the second ion gate grid than the first migration region electrode;
   wherein when the ion gate is opened, a potential well is formed between the first ion gate grid and the first migration region electrode for ionized ions so as to compress an ion group entering the migration region; and
   wherein, when the ion gate is opened, the absolute value of potential V2 of the first ion gate grid is larger than the absolute value of potential V4 of the first migration region electrode, the absolute value of potential V4 of the first migration region electrode is larger than the absolute value of potential V3 of the second ion gate grid, and the absolute value of potential V3 of the second ion gate grid is larger than or equal to the absolute value of potential V5 of the second migration region electrode.

2. The ion migration tube according to claim 1, wherein when the ion gate is opened, the absolute value of potential V2 of the first ion gate grid and the absolute value of potential V1 of the ionization region are kept constant, and the second ion gate grid is applied with a reverse pulse potential, such that the absolute value of potential V3 of the second ion gate grid is reduced by one pulse in absolute value of potential.

3. The ion migration tube according to claim 1, wherein when the ion gate is opened, absolute values of potential of electrodes of the migration region, including a first migration region electrode and a second migration region electrode, are kept the same as those in case the ion gate is closed.

4. The ion migration tube according to claim 1, wherein in case the ion gate is kept closed, the ion migration tube is configured such that the absolute value of potential V1 of the ionization region is larger than or equal to the absolute value of potential V3 of the second ion gate grid, the absolute value of potential V3 of the second ion gate grid is larger than the absolute value of potential V2 of the first ion gate grid, the absolute value of potential V2 of the first ion gate grid is larger than the absolute value of potential V4 of the first migration region electrode, and the absolute value of potential V4 of the first migration region electrode larger than the absolute value of potential V5 of the second migration region electrode.

5. The ion migration tube according to claim 4, wherein in case the ion gate is kept closed, the absolute value of potential V3 of the second ion gate grid is higher by 7~30 volts than the absolute value of potential V2 of the first ion gate grid, and a difference between the absolute value of potential V3 of the second ion gate grid and the absolute value of potential V1 of the ionization region is not greater than 50 volts.

6. A method of operating an ion migration tube, wherein the ion migration tube comprises an interior space and an ion gate disposed within the interior space and configured to be opened or closed, the interior space comprises an ionization region having an absolute value of potential V1 and a migration region isolated from the ionization region by the ion gate, so that matters enters the ion migration tube from one end of the ionization region, are ionized within the ionization region and then are driven by an electric field to enter the migration region;
   wherein, the ion gate disposed between the ionization region and the migration region comprises a first ion gate grid having an absolute value of potential V2 and a second ion gate grid having an absolute value of potential V3, the first ion gate grid and the second ion gate grid are parallel to each other and spaced apart from each other by an insulation sheet so as to divide the ion migration tube into the ionization region and the migration region; the migration region comprises at least a first migration region electrode having an absolute value of potential V4 and a second migration region electrode having an absolute value of potential V5, and the second migration region electrode is farther from the second ion gate grid than the first migration region electrode;
   wherein the method comprises, when the ion gate is opened, forming a potential well between the first ion gate grid and the first migration region electrode for ionized ions so as to compress an ion group entering the migration region; and
   wherein when the ion gate is opened, the absolute value of potential V2 of the first ion gate grid and the absolute value of potential V1 of the ionization region are kept constant, and the second ion gate grid is applied with a reverse pulse potential, such that the absolute value of potential V3 of the second ion gate grid is reduced by one pulse in absolute value of potential, thereby the absolute value of potential V2 of the first ion gate grid larger than the absolute value of potential V4 of the first migration region electrode, the absolute value of potential V4 of the first migration region electrode larger than the absolute value of potential V3 of the second ion gate grid, the absolute value of potential V3 of the second ion gate grid larger than or equal to the absolute value of potential V5 of the second migration region electrode.

7. The method according to claim 6, wherein when the ion gate is opened, absolute values of potential of electrodes of the migration region, including a first migration region electrode and a second migration region electrode, are kept the same as those in case the ion gate is closed.

8. The method according to claim 6, wherein in case the ion gate is kept closed, the ion migration tube is operated such that the absolute value of potential V1 of the ionization region is larger than or equal to the absolute value of potential V3 of the second ion gate grid, the absolute value of potential V3 of the second ion gate grid is larger than the absolute value of potential V2 of the first ion gate grid, the absolute value of potential V2 of the first ion gate grid is larger than the absolute value of potential V4 of the first migration region electrode, and the absolute value of potential V4 of the first migration region electrode larger than the absolute value of potential V5 of the second migration region electrode.

9. The method according to claim 8, wherein in case the ion gate is kept closed, the absolute value of potential V3 of the second ion gate grid is higher by 7~30 volts than the absolute value of potential V2 of the first ion gate grid, and a difference between the absolute value of potential V3 of the second ion gate grid and the absolute value of potential V1 of the ionization region is not greater than 50 volts.

* * * * *